United States Patent [19]
Bohn et al.

[11] 4,217,339
[45] Aug. 12, 1980

[54] GLYCOPROTEIN AND PROCESS FOR ISOLATING IT

[75] Inventors: Hans Bohn, Marburg an der Lahn; Wilhelm Winckler, Wenkbach, both of Fed. Rep. of Germany

[73] Assignee: Behringwerke Aktiengesellschaft, Marburg an der Lahn, Fed. Rep. of Germany

[21] Appl. No.: 903,006

[22] Filed: May 4, 1978

[30] Foreign Application Priority Data

May 7, 1977 [DE] Fed. Rep. of Germany ....... 2720704

[51] Int. Cl.$^2$ ..................... C07G 7/026; A61K 39/00
[52] U.S. Cl. ...................................... 424/12; 435/212; 435/219; 435/217; 435/226; 260/112 R; 260/112 B; 424/105
[58] Field of Search ............... 195/62, 66 R; 435/212, 435/217, 219, 226; 260/112 R, 112 B; 424/85, 12

[56] References Cited

U.S. PATENT DOCUMENTS 4,108,849  8/1978  Thomas ............................ 260/112 R

OTHER PUBLICATIONS

Gottschalk, editor, Glycoproteins, 1966.

*Primary Examiner*—Lionel M. Shapiro
*Attorney, Agent, or Firm*—Curtis, Morris & Safford

[57] ABSTRACT

What is disclosed is a glycoprotein having proteolytic, fibrinolytic, and thrombolytic properties and which can be used to prepare anti-sera useful as diagnostic agents, said glycoprotein being found in human blood serum and extracts of human placentas and being capable of isolation therefrom and which has the following properties:

- a protein proportion essentially consisting of $89\pm4\%$ of $\alpha$-amino-acids,
- a carbohydrate proportion of $11.1\pm2.2\%$, among it $5.3\pm1.1\%$ of hexoses, $2.8\pm0.5$ N of N-acetylated hexosamine, $2.9\pm0.6\%$ of N-acetylated neuraminic acid;
- a sedimentation coefficient $S_{20x}$ of $3.2\pm0.3$ S;
- a molecular weight of $32\,000\pm6\,000$;
- an iso-electric point at pH $4.3\pm0.3$;
- an extinction coefficient $E_1{}_{cm}{}^{1\%}$ (280 nm) of $13.8\pm1.0$;
- an electrophoretic mobility in the range between that of albumin and $\alpha_1$-globulins;
- a specific immunologic reaction with an antibody specifically directed against the protein, and
- a proteolytic activity, as well as a process for isolating it.

5 Claims, No Drawings

GLYCOPROTEIN AND PROCESS FOR ISOLATING IT

The present invention relates to a new glycoprotein which can be found in the blood serum and in extracts of human placentas and which can be isolated therefrom, as well as to a process for isolating it.

It is known that the protein solution obtained by aqueous extraction of human placentas contains a great number or components, which are partly serum proteins and on the other hand tissue proteins.

The task set for the present invention was to isolate a hitherto unknown glycoprotein from an extract of human placentas, to prepare with it antiserums which are specifically directed against the new glycoprotein and which permit proving the presence of the new glycoprotein in the serum qualitatively or determining it quantitatively.

Thus, the object of the invention is a new glycoprotein which can be isolated from the blood serum and the extract of human placentas. It is characterized by:

a protein proportion essentially consisting of $89\pm4\%$ of $\alpha$-amino-acids, a carbohydrate proportion of $11.1\pm2.2\%$, among it $5.3\pm1.1\%$ of hexoses, $2.8\pm0.5$ of N-acetylated hexosamine, and $2.9\pm0.6\%$ of N-acetylated neuraminic acid;

a sedimentation coefficient $S_{20x}$ of $3.2\pm0.3$ S;

a molecular weight of $32,000\pm6,000$;

an iso-electric point at pH $4.3\pm0.3$;

an extinction coefficient $E_1\ _{cm}^{1\%}$ (280 nm) of $13.8\pm1.0$;

an electrophoretic mobility in the range between that of albumin and the $\alpha_1$-globulins;

a specific immunologic reaction with an antibody specifically directed against the protein, and a proteolytic activity.

Owing to its, normally, very low concentration in human serum, it can be designated as being a trace protein.

The following explanations are given in order to clarify the characteristics of the glycoprotein:

Determination of the sedimentation coefficient was effected in an ultra-centrifuge of Messrs. Beckman (Spinco-Apparatus, type E) designed for analytical investigations, at 6000 revolutions per minute (rpm) in double sector cells with the aid of ultraviolet scanner technique at 280 nm. The solvent was a 0.05 M phosphate buffer (pH 6.8) which contained 0.2 mole/1 of NaCl. The protein concentration was 0.1%. The sedimentation coefficients were calculated on the basis of water at 20° C.

In order to determine the molecular weight, the method of the equilibrium of the sedimentation and electrophoresis in polyacrylamide gel were used. Determination in the ultracentrifuge was carried out at 9,000 rpm. The evaluation was made on the basis of a partial specific volume of 0.74 ml/g. In the ultracentrifuge, a molecular weight of $28,100\pm2,000$ was obtained.

For the electrophoresis in polyacrylamide gel, two methods were used. Separation in normal polyacrylamide (PAA)-gel was carried out according to the method of Zwisler and Biel, Z.klin. Chem. 4, page 58 (1966). For investigation in sodium dodecylsulfate-containing gel, a gel containing 7.5% of PAA and otherwise 0.1% of sodium dodecyl sulfate (SDS) was used. For reduction, the proteins were incubated in 1% of SDS with mercaptoethanol. The proteins were dyed with amido black. Upon migration within the SDS-containing PAA-gel, a molecular weight of $35,000\pm3,000$ was derived for the glycoprotein.

The determination of the iso-electric point was effected with a column (440 ml) of Messrs. LKB Stockholm. The so-called Ampholine mixture had, at the time of the investigation of the glycoprotein, a pH-value of from 3 to 5.

The test for the electrophoretic mobility was effected according to the micro-modification of Beckman Instruments on cellulose acetate foils with a sodium diethyl barbiturate buffer of pH 8.6.

Determination of the carbohydrates was carried out according to the method described by H. E. Schultze, R. Schmidtberger, H. Haupt, Biochem. Z. 329, page 490 (1958).

The analysis for amino-acids was carried out according to S. Moore, D. H. Spackmann, W. H. Stein, Anal. Chem. 30, page 1185, (1958), using the liquid chromatograph Multichrom B of Messrs. Beckman. Cystine was determined after oxidation of the proteins with performic acid (S. Moore et al., Anal. Chem. 30, page 1185, (1958)) and subsequent chromatography (S. Moore, J. Biol. Chem. 238, page 235, (1963)) as cysteinic acid. The content of tryptophan was determined by direct photometric measurement according to H. Edelhoch, Biochemistry 6, page 1948, (1967).

The immunologic characterization of the substance was effected in the most simple way according to a known diffusion process in which the antigen, i.e. the glycoprotein, and an antibody directed against the glycoprotein or antiserum which is not enriched with regard to antibodies are allowed to diffuse against each other in a carrier medium, for example agar-agar. If both reaction components meet under favorable conditions, a visible precipitate is formed. With this knowledge, it is clear to an expert, that all immunological techniques for the detection and determination of the new glycoprotein, as well as of the antibodies directed against this glycoprotein, are possible.

A simple and generally sufficiently exact method for the quantitative determination of the glycoprotein in body fluids or in tissue extracts is the so-called Laurell-technique. It is described in Analyt. Biochem. (New York), 15, page 45 (1966).

The proteolytic action of the glycoprotein was proved on fibrin agar-electrophoresis plates (N. Heimburger, G. Schwick, Protides of the Biological Fluids, 9th Coll., Bruegge, page 303 (1961)).

The present invention furthermore provides a process for isolating the above specified glycoprotein, which process is characterized by fractionating body fluids or extracts of organs which contain the glycoprotein, on the basis of the criteria found according to the invention.

The glycoprotein can be precipitated with neutral salts. With ammonium sulfate which is usually employed for such precipitations, the glycoprotein is precipitated at a saturation concentration of the salt of from 30 to 60% in pH-range in proximity of the neutral point.

According to its molecular weight, the glycoprotein can be isolated by measures which are suitable for the separation of substances with molecular weights between 2500 and 40000. It is of advantage to use for this purpose the methods of the gel-filtration or ultra-filtration.

The glycoprotein is adsorbed on weakly basic ion-exchangers at a neutral or weakly alkaline pH-value. It is of advantage to use a buffer solution which has a relatively low concentration because adsorption can be prevented by increasing the salt concentration or, also, by lowering the pH. On the other hand, knowing this behavior it is possible to adsorb the glycoprotein and then to elute it again by using more highly concentrated salt solutions or buffer solutions with lower pH-value.

It has been found that the new glycoprotein is not precipitated by the water-soluble organic bases of the acridine and quinoline series which are normally used for protein precipitation methods. At the concentrations usually employed in these processes, it remains in the aqueous supernatant. Subsequently, an acridine base, such as 2-ethoxy-6,9-diaminoacridine lactate or a quinoline base such as bis-(2-methyl-4-aminoquinolyl-6-)-carbamide-hydrochloride, can be used for the precipitation of accompanying proteins, the glycoprotein of the invention remaining in the supernatant. Similar considerations may be made when using hydroxyl-apatite as an adsorbant for proteins. The new glycoprotein shows no affinity to hydroxyl-apatite, whereas a series of accompanying proteins are fixed by hydroxyl-apatite. This behavior of the glycoprotein is characteristic, so that it is proposed to designate the glycoprotein as a hydroxyl-apatite-passing globuline (HPG-1).

On the basis of the knowledge of the electrophoretic mobility, preparative zone electrophoresis may be used for the enrichment or isolation of the glycoprotein.

The affinity of the glycoprotein, owing to its immunological behavior, may be used to enrich the glycoprotein with the aid of so-called immuno-adsorption processes. For this purpose, an immuno-adsorbant, i.e., a carrier-bound antibody directed against the new glycoprotein and which is capable of specifically binding the glycoprotein, can be prepared in a known manner. The glycoprotein can subsequently be eluted by modification of the conditions of the medium as already described in the literature.

Isolation of the substance of the present invention can thus be effected by a selected combination of the above-mentioned methods which lead, on the one hand, to an enrichment of the glycoprotein, and, on the other hand, to its separation from other accompanying proteins. Accordingly, the subject of the present invention resides in the individual steps for enriching the new glycoprotein and in the processes for its purification reached by a combination of these measures. The guideline for the process for preparing the glycoprotein consists in isolating in each case that fraction which shows a positive immunological reaction with an antiserum directed against the new glycoprotein.

After having carried out the above described process steps it has been found in some cases that the glycoprotein is still contaminated by other accompanying proteins which are immunologically detectable. Generally, these are trace proteins as the new glycoprotein itself. In this case, the contaminating substances are eliminated by their specific adsorption. For this purpose the usual methods of immuno adsorption are used in which antibodies bound to a carrier and directed against the protein to be eliminated are employed as adsorbants. In many cases, the largely-pure new glycoprotein still contains traces of the pregnancy-specific $\beta_1$-glycoprotein and/or the $\alpha$-$_1$-B-glycoprotein, which is also designated as easily precipitable $\alpha_1$-glycoprotein. For separating the last mentioned, immunoglobulins which are directed against the proteins and which are bound covalently on cross-linked agar preparations, for example SEPHAROSE, are used. The protein solution introduced into a column which has been filled with an immuno-adsorbant passes without difficulty through the column since only those components are bound against which the carrier contains an immunologically active partner. The new glycoprotein can be freed from inpurities in this manner.

For preparing the new glycoprotein, several of the measures indicated are combined with each other and only that fraction is further treated in which the new glycoprotein can be proved immunologically, whereas the remaining fractions are rejected.

As starting material for the isolation of the new glycoprotein, any body fluid or every organ extract may be used in which the glycoprotein can be proved immunologically. It is preferred to use extracts of human placentas which are obtained by comminution and extraction with water or a dilute, suitably a less than 10% strength, salt solution, advantageously with a 0.5 % strength liquid salt solution, for example sodium chloride. Suitably, about 1–5 liters of the extracted solution are used for 1 kg of placentas. The components which have not dissolved are separated from the extract by centrifugation or filtration.

The process for enriching is characterized by that at least one of the following process steps is applied to body fluids which contain the new glycoprotein and the fraction containing the glycoprotein in enriched form is isolated.

(a) Addition of water-soluble derivatives of an acridine or quinoline base, preferably 2-ethoxy-6,9-diaminoacridine-lactate in the pH-range of from 5–10, preferably at about pH 8, up to a final concentration of about 0,8% (weight to volume) the glycoprotein remaining essentially in the supernatant.

(b) Addition of neutral salts until precipitation of the glycoprotein, preferably ammonium sulfate at an about neutral pH-value of from 5–8, up to 30 to 60% of the saturation concentration of the ammonium sulfate.

(c) Adsorption of the glycoprotein on a weakly basic ion-exchanger exchanger such as diethylaminoethyl-cellulose, at a conductivity of the solution of 0–2 mS and at a neutral or weakly alkaline pH-value (6–9), for example using an about 0,01 M buffer having a pH-value of about 8. A buffer which is preferably used is, for example, tris-hydroxymethylamino-methane-HCl. Elution of the glycoprotein can be effected by lowering the pH-value below pH 7.0 or by increasing the conductivity to more than 5 mS.

(d) Separation on the basis of the size of the molecules (molecular sieve fractionation). Gel filtration in a column which is filled with a polymer of a corresponding pore size, for example epichlorohydrin-cross-linked dextran such as SEPHADEX ® produced by Messrs. Pharmacia, Uppsala, with the aim of enriching proteins with a molecular weight of about 50,000 is particularly suitable. But products such as ULTROGEL ® by Messrs. LKB, Bromma or BIO-GEL P ® produced by Bio-Rad Laboratories, Richmond, California, may likewise be used.

(e) Adsorption with hydroxyl-apatite. Since the glycoprotein is not bound by hydroxyl-apatite in dilute phosphate buffer solution, hydroxyl-apatite represents a suitable agent for removing accompanying proteins of glycoprotein from the solution. The protein solution is suitably adjusted to a pH-value around the neutral point and the conductivity of the solution is kept to about 1 mS.

(f) Preparative zone electrophoresis For carrying out an electrophoresis, a solution which contains the glycoprotein, preferably an alkaline buffer solution, for example in a sodium diethylbarbiturate buffer of pH 8.6 and anion strength of 0.1, is suitable. The solution is introduced into an apparatus for preparative electrophoresis, for example that described by N. Heimburger and R. Schmidtberger in Behringwerke Mitteilungen, Volume 43, page 83 et seq., in particular on pages 119–120. This carrier electrophoresis apparatus is horizontally arranged in an open trough, in which the carrier material is cooled to below 10° C. in order to withdraw the Joule's heat which is formed during the electrophoresis. As the carrier material, substances which are inert toward proteins, preferably polyvinyl chloride or its copolymers in the form of a fine granulate, are used.

It is recommended to carry out the electrophoresis in the alkaline pH-range, preferably at about pH 8.6, at an ion strength of 0.08–0.12 and a field strength of 4–6 volts/cm. When using 0.1 M sodium diethylbarbiturate buffer having a pH-value of 8.6, the glycoprotein migrates in an electrical field in the range of the plasma-proteins between albumin and the $\alpha_1$-globulins.

For isolating the new glycoprotein, a corresponding zone is cut out and eluted with water or aqueous salt solutions, for example an 0.5 to 1% strength sodium chloride solution, from the inert carrier material.

The protein prepared according to the invention has antigenic properties. When immunizing animals with it according to known methods, specific antibodies are formed in the blood of the immunized animals. Their sera can be isolated according to the usual methods and the antibodies contained in them can be enriched. The antisera may be used in known immunological processes for the proof and determination of the new protein in body fluids, in particular in the blood serum. In addition, the glycoprotein has proteolytic and fibrinolytic properties. A thrombolytic action and a disaggregating effect on blood platetets was likewise proved. Accordingly, the glycoprotein of the invention has properties of a valuable medicament. The following Example illustrates the invention.

EXAMPLE 150 kg of deep frozen placentas were comminuted and extracted with 150 l of a 0.5% strength aqueous sodium chloride solution. The extract was adjusted to pH 8 with 2 N-sodium hydroxide and combined with 50 l of a 3% strength aqueous solution of diaminoethoxyacridine lactate. After a dwelling time of 1 hour, the supernatant which contained the glycoprotein of the invention (HPG-1) was decanted off, combined with 5% to solid sodium chloride (11 kg) for separating the diaminoethoxyacridine lactate which still remained in solution, filtered and combined with 30%—referred to the weight of the liquid—of solid ammonium sulfate and stirred well. After 1 hour, the precipitate was filtered off.

500 g of the precipitate deposited on the filter were dissolved in 500 ml of distilled water and dialyzed against a 0.01 molar tris-(oxymethyl)-aminomethane-HCl buffer solution of a pH-value of 7.0 and which contained 0.05% sodium azide. The dialyzed solution was centrifuged and the supernatant was filled up with the same buffer solution to a volume of 2000 ml, adjusted to pH 8.0 with 0.1 N-sodiumhydroxide solution and stirred with 500 g of wet diethylaminoethyl cellulose (Messrs. SERVA, Heidelberg) for 1 hour.

The diethylaminoethyl cellulose was then separated from the solution by filtration, washed twice with 1 liter portions of 0.01 molar tris-(oxymethyl)-aminomethane-HCl buffer having a pH-value of 8.0 and eluted three times with 500 ml portions of 0.02 molar tris-(oxymethyl)-aminomethane-HCl buffer, pH 6.5, which contained 0.85% of sodium chloride and 0.05% of sodium azide.

The combined eluates were combined with 30% of ammonium sulfate, referred to the weight of the liquid, and the whole was stirred. The precipitate, which contained the glycoprotein (HPG-1), was dissolved in 300 ml of distilled water. The protein solution was dialyzed against tris-hydroxymethyl-aminomethane-HCl buffer of pH 8.0 which contained 1.0 mole of sodium chloride/liter and introduced into a column (100×20 cm) filled with SEPHADEX G-150 and eluted with the mentioned buffer. During the elution, a fractionation of the proteins according to their molecular size took place.

The eluates were subsequently tested with specific antiserum, the fractions containing the glycoprotein (HPG-1) were collected and the proteins were precipitated therefrom as described above with 30% of solid ammonium sulfate.

For further purification, the precipitate was dissolved in 50 ml of water, dialyzed against a 0.005 M phosphate buffer, pH 6.8, and introduced into a column filled with hydroxyl-apatite (size of the column 3×23 cm). Development of the column was effected with the 0.005 M phosphate buffer, pH 6.8. The glycoprotein (HPG-1) appeared in the eluate. The eluate itself was concentrated on an ultrafilter. The concentrate was then dialyzed against a 0.01 M tris-HCl-buffer, pH 7.0 and adsorbed on DEAE-SEPHADEX (column 3×23 cm). For eluting and separating the adsorbed proteins, a NaCl-gradient of 0–2% was used. The eluate fractions which contained the glycoprotein (HPG-1) were collected, concentrated, dialyzed against water and then lyophilized. About 20 mg of the new glycoprotein having a purity of >99% were obtained.

It showed the following amino-acid composition (frequency with variation coefficient (VC) in %):

|  | Frequency in Mole % | VC % |
| --- | --- | --- |
| Lysine | 0.67 | 39.25 |
| Histidine | 3.36 | 9.97 |
| Arginine | 5.09 | 6.58 |
| Aspartic acid | 5.87 | 3.07 |
| Threonine | 3.83 | 15.74 |
| Serine | 7.84 | 8.22 |
| Glutamic acid | 11.76 | 1.35 |
| Proline | 6.46 | 1.71 |
| Glycine | 10.24 | 4.49 |
| Alanine | 11.25 | 3.76 |
| Cystine/2 | 5.10 | 6.34 |
| Valine | 6.87 | 5.18 |
| Methionine | 0.42 | 14.48 |
| Isoleucine | 2.47 | 5.07 |
| Leucine | 11.42 | 4.23 |
| Tyrosine | 2.95 | 5.45 |
| Phenylalanine | 2.42 | 13.52 |
| Tryptophan | 1.98 | 11.37 |

We claim:

1. An isolated glycoprotein having the following amino acid analysis:

|  | Frequency (Mole %) | Variation Coefficient (%) |
|---|---|---|
| Lysine | 0.67 | 39.25 |
| Histidine | 3.36 | 9.97 |
| Arginine | 5.09 | 6.58 |
| Aspartic acid | 5.87 | 3.07 |
| Threonine | 3.83 | 15.74 |
| Serine | 7.84 | 8.22 |
| Glutamic acid | 11.76 | 1.35 |
| Proline | 6.46 | 1.71 |
| Glycine | 10.24 | 4.49 |
| Alanine | 11.25 | 3.76 |
| Cystine/2 | 5.10 | 6.34 |
| Valine | 6.87 | 5.18 |
| Methionine | 0.42 | 14.48 |
| Isoleucine | 2.47 | 5.07 |
| Leucine | 11.42 | 4.23 |
| Tyrosine | 2.95 | 5.45 |
| Phenylalanine | 2.42 | 13.52 |
| Tryptophan | 1.98 | 11.37 | and the following properties:
(a) a protein content of $89\pm4\%$;
(b) a carbohydrate content of $11.1\pm2.2\%$; including $5.3\pm1.1\%$ of hexoses, $2.8\pm0.5\%$ of N-acetylated hexosamine, and $2.9\pm0.6\%$ of N-acetylated neuraminic acid;
(c) a sedimentation coefficient, $S_{20,w}$, of $3.2\pm0.3$ S;
(d) a molecular weight of $32,000\pm6000$;
(e) an isoelectric point of pH $4.3\pm0.3$;
(f) an extinction coefficient, $E_{1\ cm}^{1\%}$ (280 nm), of $13.8\pm1.0$;
(g) an electrophoretic mobility in the range between albumin and the $\alpha_1$-globulins;
(h) a specific immunologic reaction with an antibody directed specifically against the glycoprotein;
(i) proteolytic activity.

2. A method for purifying a glycoprotein as in claim 1 which comprises fractionating a protein solution in which the presence of the glycoprotein can be demonstrated immunologically and isolating that fraction which contains the glycoprotein, said fractionating comprising at least one of the following steps:
  (a) adding neutral salts to said protein solution until the glycoprotein is precipitated;
  (b) fractionating said protein solution on a molecular sieve and isolating the fraction having a molecular weight between 25,000 and 40,000;
  (c) adsorbing the glycoprotein from said protein solution onto a weakly basic ion exchanger and then eluting it therefrom;
  (d) adding a water-soluble derivative of an acridine or quinoline base to said protein solution in a pH range from 5 to 10 until a final concentration of about 0.8% is reached, whereby the glycoprotein remains in said protein solution;
  (e) treating said protein solution with hydroxyl-apatite, whereby said glycoprotein remains in said protein solution;
  (f) subjecting said protein solution to preparative zone electrophoresis and isolating the zone between albumin and the $\alpha_1$-globulins; or
  (g) treating said protein solution with an immunoadsorbant.

3. A method as in claim 2 wherein said protein solution in which the presence of said glycoprotein can be demonstrated immunologically is an extract of human placentas.

4. The method of making an antiserum to the glycoprotein as in claim 1, which method comprises immunizing a vertebrate animal with said glycoprotein and then isolating that fraction of the animal's serum which contains antibodies against said glycoprotein.

5. An antiserum made by the method of claim 4.

* * * * *